US005945394A

United States Patent [19]

Sajic et al.

[11] Patent Number: 5,945,394

[45] Date of Patent: *Aug. 31, 1999

[54] HEAVY DUTY LIQUID DETERGENT COMPOSITIONS COMPRISING SALTS OF α-SULFONATED FATTY ACID METHYL ESTERS AND USE OF α-SULPHONATED FATTY ACID SALTS TO INHIBIT REDEPOSITION OF SOIL ON FABRIC

[75] Inventors: Branko Sajic, Lincolnwood; Irma Ryklin, Buffalo Grove; Arshad Malik, Mundelein, all of Ill.

[73] Assignee: Stepan Company, Northfield, Ill.

[ * ] Notice: This patent is subject to a terminal disclaimer.

[21] Appl. No.: 08/836,821

[22] PCT Filed: Sep. 17, 1996

[86] PCT No.: PCT/US96/14889

§ 371 Date: Jul. 31, 1997

§ 102(e) Date: Jul. 31, 1997

[87] PCT Pub. No.: WO97/11143

PCT Pub. Date: Mar. 27, 1997

Related U.S. Application Data

[63] Continuation of application No. 08/529,501, Sep. 18, 1995, abandoned.

[51] Int. Cl.[6] .......................... C11D 17/00; C07C 321/00

[52] U.S. Cl. .......................... 510/428; 510/352; 510/429; 510/425; 560/147

[58] Field of Search .................................... 510/351, 352, 510/357, 383, 426, 427, 428, 429, 422, 424, 425; 134/40; 560/147

[56] References Cited

U.S. PATENT DOCUMENTS

| | | | |
|---|---|---|---|
| 5,429,773 | 7/1995 | Sherry et al. | 510/444 |
| 5,616,781 | 4/1997 | Sajic et al. | 510/221 |
| 5,637,758 | 6/1997 | Sajic et al. | 560/147 |

FOREIGN PATENT DOCUMENTS

| | | |
|---|---|---|
| 0336740 | 10/1989 | European Pat. Off. . |
| 91/13959 | 9/1991 | WIPO . |

*Primary Examiner*—Necholus Ogden
*Attorney, Agent, or Firm*—McDonnell Boehnen Hulbert & Berghoff

[57] ABSTRACT

Disclosed are detergent compositions comprising:

(a) an α-sulfonated alkyl ester of a fatty acid having an average of about 12–14 carbon atoms;

(b) an anionic surfactant; and (c) a nonionic surfactant, and methods for preparing such compositions.

8 Claims, No Drawings

HEAVY DUTY LIQUID DETERGENT COMPOSITIONS COMPRISING SALTS OF α-SULFONATED FATTY ACID METHYL ESTERS AND USE OF α-SULPHONATED FATTY ACID SALTS TO INHIBIT REDEPOSITION OF SOIL ON FABRIC

BACKGROUND OF THE INVENTION

This application is a continuation-in-part of U.S. application Ser. No. 08/529,501, filed Sep. 18, 1995, now abandoned.

FIELD OF THE INVENTION

The present invention relates to detergent compositions comprising one or more anionic sulfate or sulfonate surfactants. More particularly, the invention relates to heavy duty liquid detergent compositions comprising a sulfonated alkyl ester, at least one primary anionic surfactant, and nonionic surfactant. It relates to detergent compositions which possess desirable cleaning and sudsing properties, are mild, and are especially suitable for use in manual and machine laundry applications.

DESCRIPTION OF THE RELATED ART

Heavy duty liquid (HDL) detergent compositions are intended to clean clothes made of cotton, polyester, wool, cotton/polyester blends, silk, etc. HDL detergents typically fall into one of three categories: built detergents, unbuilt detergents, and detergents for fine fabric cold water washing.

Unbuilt products, i.e., those containing no builder, are composed of anionic surfactants, typically linear alkyl benzene sulfonates (LAS), ether sulfate, and a nonionic surfactant typically a fatty alcohol ethoxylate. The function of anionic surfactants is to remove and suspend particulate soil while nonionic solubilizes, disperses and emulsifies oily soil. The systems utilizing LAS usually have poor cleaning performance, this is especially true in hard water.

Built HDL systems, i.e., detergents having builders, contain surfactants in addition to a certain level of builder. Builders function to protect the surfactant, in particular LAS, alkyl sulfate, and alpha olefin sulfonate, from precipitating in dilute or hard water. In addition, builders are good sources of alkalinity and help improve cleaning performance. Despite incorporation of builders in such compositions, their cost/performance efficiency has major shortfall.

To minimize the shelf space required for displaying detergent products, many attempts have been made to prepare cost efficient, highly concentrated detergents having good cleaning at use concentration.

Preparation of concentrated products having high levels of surfactants requires higher levels of hydrotrope to fluidize the composition. However, concentrating product via incorporation of high levels of builder into the detergent increases the cost of manufacturing as well as increases the difficulty of dispersion and disolution especially in cold water. Some highly built products are in the form of structured liquid and have an appearance similar to that of fabric softeners.

Thus, there exists a need for highly concentrated heavy duty liquid detergent compositions that do not require the presence of builder for cleaning efficiency or classical hydrotrope for fluidity and that are capable of providing good cleaning of fabrics at low use concentrations and especially in cold to warm temperature washing conditions.

SUMMARY OF THE INVENTION

The compositions of the present invention are cost efficient unbuilt concentrated heavy duty liquid detergents with high cleaning efficacy comprising:

(a) a salt of sulfonated alkyl ester;

(b) an anionic surfactant; and (c) a nonionic surfactant.

The invention provides HDL detergents that do not require the presence of builders for improved cleaning efficiency. The invention further provides fluid HDL detergents that do not require the addition of classical hydrotopes. The inventive highly concentrated, stable fluid compositions are highly surface active and very effective in cleaning a variety of fabrics with different types of soils at a low use concentration in water and perform extremely well even under cold temperature washing conditions. The compositions of the present invention show anti-redeposition properties which makes them especially useful for cleaning non-polar synthetic fabrics and blends of synthetic and natural fabrics. In addition, the inventive compositions when combined with silicone, fatty acid soaps and EO/PO/EO or PO/EO/PO block copolymer defoamers are very useful in front loading European style washing machines. Furthermore, the inventive compositions exhibit excellent surface activity and extremely low CMC's (critical micelle concentration) which demonstrates synergy between the sulfonated alkyl esters and the other surfactants. This synergistic behavior of the inventive compositions contributes towards significant improvement in cleaning efficiency at equal surfactant concentrations when compared under similar conditions with state-of-the art commercial products. When used at lower active concentrations, these inventive compositions give equal performance to the state-of-the art commercial products thus realizing significant cost savings.

The inventive concentrated compositions have suitable viscosities and are clear liquids in the concentrated and diluted forms.

The invention also provides concentrated compositions having an amount of a disalt α-sulfonated alkyl acid effective to provide for improved cleaning efficacy with respect to antiredeposition of soils, etc. In this context, the compositions comprising disalts of alpha sulfonated fatty acids act as antiredeposition cleaning compositions.

DETAILED DESCRIPTION OF THE INVENTION

The invention provides detergent compositions comprising a salt of an alpha sulfonated alkyl ester of a fatty acid, an anionic surfactant, and a nonionic surfactant. The anionic surfactant is selected from the group consisting of linear alkyl benzene sulfonates, alkyl sulfates, alkyl ethoxy sulfates, alpha-olefin sulfonates, paraffin sulfonates, alkyl glyceryl ether sulfonates, secondary alkane sulfonates, acyl-N-($C_1$–$C_4$ alkyl) or —N—($C_2$–$C_4$ hydroxyalkyl) glucamine sulfates, $C_8$–$C_{18}$ alkyl sulfoacetates and $C_8$–$C_{18}$ secondary alcohol sulfates and mixtures thereof. In the detergent mixture, a combination of methyl ester sulfonate and an anionic surfactant and are normally present at ratios of from about nil to nonionic 4:1 to 1:4. The sum of the concentrations of α-sulfonated alkyl ester, anionic surfactant, and nonionic surfactant in a washing solution ranges from about 0.05% to about 3.0% by weight. In addition, the detergent composition is a liquid having a viscosity of from about 150–1000 cps at 25° C.

The nonionic surfactant is typically an amide, alkyl n-methyl glucamine, amine oxide, $C_8$–$C_{18}$ fatty alcohol ethoxylates, ethoxylated methyl esters, nonyl phenyl ethoxylates or mixtures thereof.

It has been unexpectedly discovered that when an alpha sulfonated alkyl ester of a fatty acid is combined in a detergent composition with an anionic surfactant and a combination of sulfonated methyl ester and an nonionic surfactant at a weight ratio of total anionic surfactant to nonionic of 5:1 to 1:3, the composition demonstrates surprisingly efficient cleaning at dilute concentrations and is fluid at high concentrations.

It has further been discovered that when the alpha sulfonated alkyl ester component includes a certain amount of a disalt of alpha sulfonated fatty acid, the formulation provides improved cleaning of substrates in terms of less redeposition of the soils, grease, etc. to be removed. In this context, the disalts of alpha sulfonated fatty acids act as antiredeposition agents.

In one embodiment, the invention comprises detergent compositions which comprise:

(a) a mono-salt of an alpha-sulfonated methyl ester of a fatty acid having from 8–20 carbon atoms and a di-salt of an alpha-sulfonated fatty acid, the ratio of mono-salt to di-salt being at least about 2:1;

(b) an anionic surfactant selected from the group consisting of linear alkyl benzene sulfonates where the alkyl portion has from about 8 to 15 carbon atoms, alkyl sulfate where the alkyl portion has from about 8 to 18 carbon atoms, alkyl ethoxy sulfates where the alkyl portion has from about 8 to 18 carbon atoms and the average degree of ethoxylation is from about 1 to 7, alpha-olefin sulfonates where the olefin portion is a straight or branched chain unsaturated hydrocarbon having from 8 to 24 carbon atoms, paraffin sulfonate having from 8 to 18 carbon atoms, $C_9$–$C_{20}$ alkyl glyceryl ether sulfonates, $C_8$–$C_{18}$ secondary alkane sulfonates, $C_9$–$C_{17}$ acyl-N-($C_1$–$C_4$ alkyl) or -N-($C_2$–$C_4$ hydroxyalkyl) glucamine sulfates, $C_8$–$C_{18}$ alkyl sulfoacetates and $C_8$–$C_{18}$ secondary alcohol sulfates and mixtures thereof; and (c) a nonionic surfactant.

In certain embodiments of the invention, the detergent compositions comprise:

(a) a salt of a alpha-sulfonated methyl ester of a fatty acid having from about 8 to 18 carbon atoms;

(b) a salt of a alkyl ethoxy sulfate where the alkyl portion has about 8 to 18 carbon atoms and the average degree of ethoxylation is from about 1 to 7; and (c) a nonionic surfactant where the composition comprises at least about 3.5:1 by weight of surfactant.

Alpha-Sulfonated Alkyl Ester

The alpha-sulfonated alkyl ester is present in the inventive concentrated compositions at concentrations of from about 1–50% by weight. Preferred compositions contain about 2–35% by weight sulfonated alkyl ester and more preferred compositions contain about 2–20% by weight of the sulfonated alkyl ester.

The alpha-sulfonated alkyl ester employed in the inventive compositions may be pure alkyl ester or a blend of (1) a mono-salt of an alpha-sulfonated alkyl ester of a fatty acid having from 8–20 carbon atoms where the alkyl portion forming the ester is straight or branched chain alkyl of 1–6 carbon atoms and (2) a disalt of an alpha-sulfonated fatty acid, the ratio of mono-salt to di-salt being at least about 2:1, and up to about 25:1. The alpha-sulfonated alkyl esters used in the invention are typically prepared by sulfonating an alkyl ester of a fatty acid with a sulfonating agent such as $SO_3$. When prepared in this manner, the alpha-sulfonated alkyl esters normally contain a minor amount, typically not exceeding 33% by weight, of the di-salt of the alpha-sulfonated fatty acid which results from hydrolysis of the ester. Preferred alpha-sulfonated alkyl esters contain less than about 10% by weight of the di-salt of the corresponding alpha-sulfonated fatty acid.

Preferred compositions according to the invention comprise a mixture of mono-salt and di-salt of the alpha sulfonated fatty acid. Most preferred compositions contain about 4–10% by weight of the mono-salt of methyl alpha sulfonated fatty ester. The compositions preferably contain from about 0.01–20%, more preferably 0.2–10%, and most preferably 0.3–5%, by weight of the di-salt of the alpha-sulfonated fatty acid.

In particularly preferred compositions comprising such mixtures, the amount of mono-salt should be sufficient to solubilize the di-salt. Alternatively, the di-salt may be solubilized using other surfactants, e.g., anionic or nonionic surfactants, or traditional hydrotropes, although heating may be required during manufacture. In such compositions, the dissolved di-salt of the alpha sulfonated fatty acid functions as an antiredeposition agent.

The alpha-sulfonated alkyl esters, i.e., alkyl ester sulfonate surfactants, include linear esters of $C_8$–$C_{20}$ carboxylic acid (i.e., fatty acids) which are sulfonated with gaseous $SO_3$ according to the "The Journal of American Oil Chemists Society," 52 (1975), pp. 323–329. Suitable starting materials would include natural fatty substances as derived from tallow, palm oil, coconut etc.

The preferred alkyl ester sulfonate or fatty acid alpha sulfonate surfactants comprise alkyl sulfonate surfactants of the structural formula:

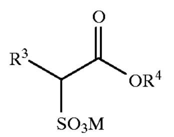

wherein $R_3$ is a $C_8$–$C_{20}$ hydrocarbyl, preferably an alkyl, or combination thereof, $R_4$ is hydrogen or a straight or branched chain $C_1$–$C_6$ hydrocarbyl, preferably an alkyl, or combination thereof, and M is a cation which forms a water soluble salt with the alkyl ester sulfonate. Suitable salt-forming cations include metals such as calcium, magnesium, sodium, potassium, and lithium, and substituted or unsubstituted ammonium cations, such as monoethanol amine, diethanolamine, and triethanolamine. Preferably, $R_3$ is $C_{10}$–$C_{16}$ alkyl, and $R_4$ is methyl, ethyl or isopropyl. More preferred are alpha-sulfonated methyl esters of mixtures of fatty acids having an average of from 12 to 16 carbon atoms. Most preferred are alpha-sulfonated methyl and ethyl esters of mixtures of fatty acids having an average of from about 12 to 14 carbon atoms. A particularly preferred mixture has an average of about 13.6 carbon atoms in the fatty acid portion. When $R_4$ is hydrogen in the above formula, the formula represents a di-salt of an alpha sulfonated fatty acid.

Anionic Surfactant

Anionic surfactants can be selected from the following: alkyl benzene sulfonates, alkyl sulfates, alkyl ethoxy sulfates, paraffin sulfonates, monoalkane sulfonates, olefin sulfonates, and alkyl glyceryl sulfonates. The anionic surfactant is present in the detergent at concentrations of from 1–50%, preferably from about 2–30%, and most preferably from about 2–25%, by weight of the detergent composition.

Alkyl benzene sulfonates useful in compositions of the present invention are those in which the alkyl group, which is substantially linear, contains 8–15 carbon atoms, preferably 10–13 carbon atoms, a material with an average carbon chain length of about 11.5 being most preferred. The phenyl isomer distribution, i.e., the point of attachment of the alkyl chain to the benzene nucleus, is not critical, but alkyl benzenes having a high 2-phenyl isomer content are preferred.

Suitable alkyl sulfates are primary alkyl sulfates in which the alkyl group contains 8–18 carbon atoms, more preferably an average of 12–14 carbon atoms preferably in a linear chain. $C_{10}$–$C_{16}$ alcohols, derived from natural fats, or Ziegler olefin build-up, or OXO synthesis, form suitable sources for the alkyl group. Examples of synthetically derived materials include Dobanol 23 (RTM) sold by Shell Chemicals (UK) Ltd., Ethyl 24 sold by the Ethyl Corporation, a blend of $C_{13}$–$C_{15}$ alcohols in the ratio 67% $C_{13}$, 33% $C_{15}$ sold under the trade name Lutensol by BASF GmbH and Synperonic (RTM) by ICI Ltd., and Lial 125 sold by Liquichimica Italina. Examples of naturally occurring materials from which the alcohols can be derived are coconut oil and palm kernel oil and the corresponding fatty acids.

Alkyl ethoxy sulfate surfactants comprise a primary alkyl ethoxy sulfate derived from the condensation product of a $C_8$–$C_{22}$ alcohol with an average of up to 25 ethylene oxide groups. The $C_8$–$C_{22}$ alcohol itself can be obtained from any of the sources previously described for the alkyl sulfate component. $C_{12}$–$C_{13}$ alkyl ethoxy sulfates are preferred as primary anionic surfactants where the average degree of ethoxylation is about 3.

Conventional base-catalyzed ethoxylation processes to produce an average degree of ethoxylation of 12 result in a distribution of individual ethoxylates ranging from 1 to 15 ethoxy groups per mole of alcohol, so that the desired average can be obtained in a variety of ways. Blends can be made of material having different degrees of ethoxylation and/or different ethoxylate distributions arising from the specific ethoxylation techniques employed and subsequent processing steps such as distillation. In preferred compositions in accordance with the present invention as alkyl ethoxy sulfate is used with has an average degree of ethoxylation of from 0.4 to 6.5, more preferably from 2 to 4.

Paraffin sulfonates are also useful in the present invention and have from 8 to 18 carbon atoms per molecule, more desirably 13 to 16 carbon atoms per molecule. These sulfonates are preferably prepared by subjecting a cut of paraffin, corresponding to the chain length specified above, to the action of sulfur dioxide and oxygen in accordance with the well-known sulfoxidation process. The product of this reaction is a secondary sulfonic acid which is then neutralized with a suitable base to provide a water-soluble secondary alkyl sulfonate. Similar secondary alkyl sulfonates may be obtained by other methods, i.e. by the sulfochlorination method in which chlorine and sulfur dioxide are reacted with paraffins in the presence of actinic light, the resulting sulfonyl chlorides being hydrolyzed and neutralized to form the secondary alkyl sulfonates. Whatever technique is employed, it is normally desirable to produce the sulfonate as the monosulfonate, having no unreacted starting hydrocarbon or having only a limited proportion thereof present and with little or no inorganic salt by-product. Similarly, the proportions of disulfonate or higher sulfonated material will be minimized, although some may be present. The monosulfonate may be terminally sulfonated or the sulfonate group may be joined on the 2-carbon or other carbon of the linear chain. Similarly, any accompanying disulfonate, usually produced when an excess of sulfonating agent is present, may have the sulfonate groups distributed over different carbon atoms of the paraffin base, and mixtures of the monosulfonates and disulfonates may be present.

Mixtures of monoalkane sulfonates wherein the alkanes are of 14 and 15 carbon atoms are particularly preferred wherein the sulfonates are present in the weight ratio of $C_{14}$–$C_{15}$ paraffins in the range of 1:3 to 3:1.

Olefin sulfonates useful in the present invention are mixtures of alkene-1-sulfonates, alkene hydroxysulfonates, alkene disulfonates and hydroxydisulfonates, and are described in the commonly assigned U.S. Pat. No. 3,332,880, issued to P. F. Pflauner and A. Kessler on Jul. 25, 1967.

Suitable alkyl glyceryl ether sulfonates are those derived from ethers of coconut oil and tallow.

Other sulfate surfactants include the $C_8$–$C_{17}$ acyl-N-($C_1$–$C_4$ alkyl) -N-($C_1$–$C_2$ hydroxyalkyl) glucamine sulfates, preferably those in which the $C_8$–$C_{17}$ acyl group is derived from coconut or palm kernel oil. These materials can be prepared by the method disclosed in U.S. Pat. No. 2,717,894, issued Sep. 13, 1955 to Schwartz.

The counterion for the anionic surfactant component may be any cation capable of forming a water soluble salt. Representative counterions include, for example, $Na^+$, $K^+$, divalent cations such as $Mg^{++}$ and $Ca^{++}$, $Al^{3+}$, ammonium and substituted ammonium such as alkanolammonium. Suitable alkanolammonium ions include those formed from mono-, di-, and triethanolamines. Preferred counterions are divalent cations, such as, for example, magnesium and calcium magnesium is a particularly preferred counterion for the anionic surfactant.

Nonionic Surfactant

The detergent compositions of the present invention also comprise from about 1% to about 50%, preferably from about 2% (more preferably 8 to 20%) to about 40% by weight of a foam stabilizing surfactant selected from the group consisting of amides, amine oxides, ethoxylated fatty acids, $C_8$–$C_{18}$ fatty alcohol ethoxylates, alkyl polyglycosides, alky n-methyl glucamides, nonyl phenyl ethoxylates, methyl eater ethoxylates and mixtures thereof.

Amine oxides useful in the present invention include long-chain alkyl amine oxides, i.e., those compounds having the formula

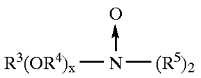

wherein $R^3$ is selected from an alkyl, hydroxyalkyl, acylamidopropyl and alkyl phenyl group, or mixtures thereof, containing from 8 to 26 carbon atoms, preferably 8 to 16 carbon atoms; $R^4$ is an alkylene or hydroxyalkylene group containing from 2 to 3 carbon atoms, preferably 2 carbon atoms, or mixtures thereof; x is from 0 to 3, preferably 0; and each $R^5$ is an alkyl or hydroxyalkyl group containing from 1 to 3, preferably from 1 to 2 carbon atoms, or a polyethylene oxide group containing from 1 to 3, preferably 1, ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxyethyl amine oxides. Examples of such materials include dimethyloctylamine oxide, diethyldecylamine oxide, bis-(2-hydroxyethyl) dodecylamine oxide, dimethyldodecylamine oxide, dodecylamidopropyl dimethylamine oxide and dimethyl-2-hydroxyoctadecylamine oxide. Preferred are $C_{10}$–$C_{18}$ alkyl dimethylamine oxide, and $C_{10}$–$C_{18}$ acylamido alkyl dimethylamine oxide.

The nonionic surfactant may also be a fatty acid amide surfactant. Preferred amides are $C_8$–$C_{20}$ alkanol amides, monoethanolamides, diethanolamides, and isopropanolamides. A particularly preferred amide is a mixture of myristic monoethanolamide and lauric monoethanolamide. This preferred amide is sold by Stepan Company, Northfield, Ill. as Ninol LMP.

Other suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from 6 to 12 carbon atoms in either a straight-or branched-chain configuration with the alkylene oxide. In a preferred embodiment, the ethylene oxide is present in an amount equal to from about 5 to about 25 moles of ethylene oxide per mole of alkyl phenol. Commercially available nonionic surfactants of this type include Igepal™ CO-630, marketed by the GAF Corporation; and Triton™ X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from about 10 to about 20 carbon atoms with from about 2 to about 10 moles of ethylene oxide per mole of alcohol. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-6.5 (the condensation product of $C_{12}$–$C_{13}$ linear alcohol with 6.5 moles of ethylene oxide), Neodol™ 45-7 (the condensation product of $C_{14}$–$C_{15}$ linear alcohol with 7 moles of ethylene oxide), Neodol™ 45-4 (the condensation product of $C_{14}$–$C_{15}$ linear alcohol with 4 moles of ethylene oxide), marketed by Shell Chemical Company, and Kyro™ EOB (the condensation product $C_{13}$–$C_{15}$ alcohol with 9 moles ethylene oxide), marketed by The Procter & Gamble Company.

3. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of propyloxyethylene and has a molecular weight of from about 5,000 to about 11,000. Examples of this type of nonionic surfactant include certain of the commercially available Tetronic™ compounds, marketed by BASF.

5. Semi-polar nonionic surfactants are a special category of nonionic surfactants which include water-soluble amine oxides containing one alkyl moiety of from 10 to 18 carbon atoms and 2 moieties selected from the group consisting of alkyl groups and hydroxyalkyl groups containing from 1 to 3 carbon atoms; and water-soluble sulfoxides containing one alkyl moiety of from 10 to 18 carbon atoms and a moiety selected from the group consisting of alkyl and hydroxyalkyl moieties of from 1 to 3 carbon atoms.

Semi-polar nonionic detergent surfactants include the amine oxide surfactants. These amine oxide surfactants in particular include $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565, 647, Llenado, issued Jan. 21, 1986, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from 8 to 18, preferably from 12 to 14 carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolethoxdy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

Optional ingredients include detergency builders, either of the organic or inorganic type, although such builders in general are not preferred for use in the composition of the present invention. Examples of water-soluble inorganic builders which can be used, either alone or in admixture with themselves or with organic alkaline sequentrant builder salts, are glycine, alkyl and alkenyl succinates, alkali metal carbonates, alkali metal bicarbonates, phosphates, polyphosphates, and silicates. Specific examples of such salts are sodium tripolyphosphate, sodium carbonate, potassium carbonate, sodium bicarbonate, potassium bicarbonate, sodium pyrophosphate, potassium pyrophosphate. Examples of organic builder salts which can be used alone, or in admixture with each other, or with the preceding inorganic alkaline builder salts, are alkali metal polycarboxylates, examples of which include but are not limited to, water-soluble citrates such as sodium and potassium citrate, sodium and potassium tartrate, sodium and potassium ethylenediaminetetracetate, sodium and potassium N-(2hydroxyethyl)-nitrilo triacetates, sodium and potassium N-(2hydroxyethyl)-nitrilo diacetates, sodium and potassium oxydisuccinates, and sodium and potassium tartrate mono- and di-succinates, such as those described in U.S. Pat. No. 4,663,071 (Bush et al., issued May 5, 1987), the disclosure of which is; incorporated herein. Other organic detergency builders, such as; water-soluble phosphonates, can be used in the compositions of the present invention. However, detergency builders in general have limited value when the compositions of the present invention are in the form of heavy-duty liquid or light-duty liquid dishwashing detergent compositions. If included in the compositions of the present invention, these optional builders are typically present at a concentration of from about 1.0% to about 10%, preferably from about 2% to about 5% by weight.

Other optional ingredients include diluents, solvents, dyes, perfumes and hydrotropes. Diluents can be inorganic salts, such as sodium and potassium sulfate, ammonium chloride, sodium and potassium chloride, sodium bicarbonate, etc. Diluents useful in the compositions of the present invention are typically present at levels of from about 1% to about 10%, preferably from about 2% to about 5% by weight.

Solvents useful herein include water and lower molecular weight alcohols, such as ethyl alcohol, isopropyl alcohol, etc. Solvents useful in the compositions of the present invention are typically present at levels of from about 1% to about 60%, preferably from about 5% to about 50% by weight.

Traditional hydrotropes such as sodium and potassium toluene sulfonate, sodium and potassium xylene sulfonate, sodium and potassium cumene sulfonate, trisodium and tripotassium sulfosuccinate, and related compounds (as disclosed in U.S. Pat. No. 3,915,903, the disclosure of which is incorporated herein) can be utilized in the compositions. Although such hydrotropes may be used, they are not normally needed in the inventive compositions. Preferred compositions do not include traditional hydrotropes since they do not contribute towards the cleaning and grease-cutting capabilities of the compositions. Thus, preferred compositions are substantially free from traditional hydrotropes based on (1) aromatic sulfonates and (2) sulfonated carboxylic acids.

The cleaning compositions may also contain one or more polyhydroxy fatty acid amides having the structural formula:

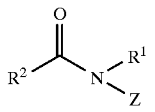

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight-chain $C_7$–$C_{19}$ alkyl or alkenyl, more preferably straight-chain $C_9$–$C_{17}$ alkyl or alkenyl, most preferably straight-chain $C_1$–$C_{17}$ alkyl or alkenyl, or mixture thereof; and Z is a polyhydroxyhydrocarbyl having a linear hydrocarbyl chain with at least 3 hydroxyls directly connected to the chain, or an alkylated derivative (preferably ethoxylated or propoxylated) thereof. Z preferably will be derived from a reducing sugar in a reductive amination reaction; more preferably Z is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of $—CH_2—(CHOH)_n—CH_2OH$, $—CH(CH_2OH)-(CHOH)_n—CH2OH$, $—CH_2—(CHOH)_2(CHOR')-CH_2OH$, where n is an integer from 3 to 5, inclusive, and $R^1$ is H or a cyclic or aliphatic monosaccharide, and alkoxylated derivatives thereof. Most preferred are glycityls wherein n is 4, particularly $—CH_2-(CHOH)_4—CH_2OH$.

$R^1$ can be, for example, N-methyl, N-ethyl, N-propyl, N-isopropyl, N-butyl, N-2-hydroxy ethyl, or N-2-hydroxy propyl.

$R^2$-CO-N< can be, for example, cocamide, stearamide, oleamide, lauramide, myristamide, capricamide, palmitamide, tallowamide, etc. Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The detergent compositions hereof may contain bleaching agents or bleaching compositions containing bleaching agent and one or more bleach activators. When present bleaching compounds will typically be present at levels of from about 1% to about 20%, more typically from about 1% to about 10%, of the detergent composition. In general, bleaching compounds are optional components in non-liquid formulations, e.g., granular detergents. If present, the amount of bleach activators will typically be from about 0.1% to about 60%, more typically from about 0.5% to about 40% of the bleaching composition.

The bleaching agents used herein can be any of the bleaching agents useful for detergent compositions in textile cleaning, hard surface cleaning, or other cleaning purposes that are now known or become known. These include oxygen bleaches as well as other bleaching agents. For wash conditions below about 50° C., especially below about 40° C., it is preferred that the compositions hereof not contain borate or material which can form borate in situ (i.e., borate-forming material) under detergent storage or wash conditions. Thus it is preferred under these conditions that a non-borate, non-borate-forming bleaching agent is used. Preferably, detergents to be used at these temperatures are substantially free of borate and borate-forming material. As used herein, "substantially free of borate and borate-forming material" shall mean that the composition contains no more than about 2% by weight of borate-containing and borate-forming material of any type, preferably, no more than 1%, more preferably 0%.

One category of bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application Ser. No. 740,446, Burne et al., filed Jun. 3, 1985, European Patent Application 0,133,354, Banks et al., published Feb. 20, 1985, and U.S. Pat. No. 4,412,934, Chung et al., issued Nov. 1, 1983, all of which are incorporated by reference herein. Highly preferred bleaching agents also include 6-nonylamino-6-oxoperoxycaproic acid as described in U.S. Pat. No. 4,634,551, issued Jan. 6, 1987 to Burns, et al., incorporated herein by reference.

Another category of bleaching agents that can be used encompasses the halogen bleaching agents. Examples of hypohalide bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

Peroxygen bleaching agents can also be used. Suitable peroxygen bleaching compounds include sodium carbonate peroxyhydrate, sodium pyrophosphate peroxyhydrate, urea peroxyhydrate, and sodium peroxide.

Peroxygen bleaching agents are preferably combined with bleach activators, which lead to the in situ production in aqueous solution (i.e., during the washing process) of the peroxy acid corresponding to the bleach activator.

Preferred bleach activators for incorporation into compositions of the present invention are described in U.S. Pat. No. 4,915,854, issued Apr. 10, 1990 to Man, et al., incorporated herein by reference, and U.S. Pat. No. 4,412,934, which was previously incorporated herein by reference.

Bleaching agents other than oxygen bleaching agents are also known in the art and can be utilized herein. One type of nonoxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanines and a photoactivated bleaching process are described in U.S. Pat. No. 4, 033,718, issued Jul. 5, 1977 to Holcombe et al., incorporated herein by reference. Typically, detergent compositions will contain about 0.025% to about 1.25% by weight, of sulfonated zinc phthalocyanine.

Any polymeric soil release agents known to those skilled in the art can be employed in the practice of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

By "soil release agent-enhancing amount" of polyhydroxy fatty acid amide is meant an amount of such surfactant that will enhance deposition of the soil release agent upon hydrophobic grease/oil cleaning performance can be obtained for fabrics washed in the detergent composition hereof in the next subsequent cleaning operation.

The amount of polyhydroxy fatty acid amide needed to enhance deposition will vary with the anionic surfactant selected, the amount of anionic surfactant, the particular soil release agent chosen, as well as the particular polyhydroxy fatty acid amide chosen. Generally, compositions will comprise from about 0.01% to about 10%, by weight, of the polymeric soil release agent, typically from about 0.1% to about 5%, and from about 4% to about 50%, more typically from about 5% to about 30% of anionic surfactant. Such compositions should generally contain at least about 1%, preferably at least about 3%, by weight, of the polyhydroxy fatty acid amide, though it is not intended to necessarily be limited thereto.

The polymeric soil release agents for which performance is enhanced by polyhydroxy fatty acid amide in the presence of anionic surfactant include those soil release agents having: (a) one or more nonionic hydrophile components consisting essentially of (1) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate: $C_3$ oxyalkylene terephthalate units is about 2:1 or lower, (ii) $C_4$–$C_6$ alkylene or oxy $C_4$–$C_6$ alkylene segments, or mixtures thereof, (iii) poly (vinyl ester) segments, preferably poly(vinyl acetate), having a degree of polymerization of at least 2, or (iv) $C_1$–$C_4$ alkyl ether or $C_4$ hydroxyalkyl ether substituents, or mixtures thereof, wherein said substituents are present in the form of $C_1$–$C_4$ alkyl ether or $C_4$ hydroxyalkyl ether cellulose derivatives, or mixtures thereof, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from 2 to about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988 to Gosselink, incorporated herein by reference.

Polymeric soil release agents useful in the present invention include cellulosic derivatives such as hydroxyether cellulosic polymers, copolymeric blocks of ethylene terephthalate or propylene terephthalate with polyethylene oxide or polypropylene oxide terephthalate, and the like.

Cellulosic derivatives that are functional as soil release agents are commercially available and include hydroxyethers of cellulose such as Methocel® (Dow).

Cellulosic soil release agents for use herein also include those selected from the group consisting of $C_1$–$C_4$ alkyl and $C_4$ hydroxyalkyl cellulose such as methylcellulose, ethylcellulose, hydroxypropyl methylcellulose, and hydroxybutyl methylcellulose. A variety of cellulose derivatives useful as soil release polymers are disclosed in U.S. Pat. No. 4,000,093, issued Dec. 28, 1976 to Nicol, et al., incorporated herein by reference.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. Such materials are known in the art and are desribed in European Patent Application 0 219 048, published Apr. 22, 1987 by Kud, et al. Suitable commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. More specifically, these polymers are comprised of repeating units of ehtylene terephthalate and PEO terephthalate in a mole ratio of ethylene terephthalate units to PEO terephthalate units of from about 25:75 to about 35:65, said PEO terephthalate units containing polyethylene oxide having molecular weights of from about 300 to about 2000. The molecular weight of this polymeric soil release agent is in the range of from about 25,000 to about 55,000. See U.S. Pat. No. 3,959,230 to Hays, issued May 25, 1976, which is incorporated by reference. See also U.S. Pat. No. 3,893,929 to Basadur issued Jul. 8, 1975 (incorporated by reference) which discloses similar copolymers.

Another preferred polymeric soil release agent is a polyester with repeat units of ehtylene terephthalate units containing 10–15% by weight of ethylene terephthalate units together with 90–80% by weight of polyoxyethylene terephthalate units, derived from a polyoxyethylene glycol of average molecular weight 300–5,000, and the mole ratio of ethylene terephthalate units to polyoxyethylene terephthalate units in the polymeric compound is between 2:1 and 6:1. Examples of this polymer include the commercially available material ZELCON 5126 (from DuPont) and MILEASE T (from ICI). These polymers and methods of their preparation are more fully described in U.S. Pat. No. 4,702,857, issued Oct. 27, 1987 to Gosselink, which is incorporated herein by reference.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone, said soil release agent being derived from allyl alcohol ethoxylate, dimethyl terephthalate, and 1,2 propylene diol, wherein after sulfonation, the terminal moieties of each oligomer have, on average, a total of from about 1 to about 4 sulfonate groups. These soil release agents are described fully in U.S. Pat. No. 5,958,451, issued Nov. 6, 1990 to J. J. Scheibel and E. P. Gosselink, U.S. Ser. No. 07/474,709, filed Jan. 29, 1990, incorporated herein by reference.

Other suitable polymeric soil release agents include the ethyl- or methyl-capped 1,2-propylene terephthalatepolyoxyethylene terephthalate polyesters of U.S. Pat. No. 4,711,730, issued Dec. 8, 1987 to Gosselink et al., the anionic end-capped oligomeric esters of U.S. Pat. No. 4,721,580, issued Jan. 26, 1988 to Gosselink, wherein the anionic end-caps comprise sulfo-polyethoxy groups derived from polyethylene glycol (PEG), the block polyester oligomeric compounds of U.S. Pat. No. 4,702,857, issued Oct. 27, 1987 to Gosselink, having polyethoxy end-caps of the formula $X\text{-}(OCH_2CH_2)_n$— wherein n is from 12 to about 43 and X is a $C_1$–$C_4$ alkyl, or preferably methyl, all of these patents being incorporated herein by reference.

Additional polymeric soil release agents include the soil release agents of U.S. Pat. No. 4,877,896, issued Oct. 31, 1989 to Maldonado et al, which discloses anionic, especially sulfoaruyl, end-capped terephthalate esters, said patent being incorporated herein by reference. The terephthalate esters contain unsymmetrically substituted oxy-1,2-alkylenoxy units. Included among the soil release polymers of U.S. Pat. No. 4,877,896 are materials with polyoxyethylene hydrophile components of $C_3$ oxyalkylene terephthalate (propylene terephthalate) repeat units within the scope of the hydrophobe components of (b)(i) above. It is the polymeric soil release agents characterized by either, or both, of these criteria that particularly benefit from the inclusion of the polyhydroxy fatty acid amides hereof, in the presence of anionic surfactants.

If utilized, soil release agents will generally comprise from about 0.01% to about 10.0%, by weight, of the detergent compositions herein, typically from about 0.1% to about 5%, preferably from about 0.2% to about 3.0%.

Chelating Agents

The detergent compositions herein may also optionally contain one or more iron and manganese chelating agents as a builder adjunct material. Such chelating agents can be selected from the group consisting of amino carboxylates, amino phosphonates, polyfunctionally-substituted aromatic chelating agents and mixtures thereof, all as hereinafter defined. Without intending to be bound by theory, it is believed that the benefit of these materials is due in part to their exceptional ability to remove from and manganese ions from washing solutions by formation of soluble chelates.

Amino carboxylates useful as optional chelating agents in compositions of the invention include, for example, ethylenediamietetraacetates, N-hydroxyethylethyleneiaminetriacetates, nitrilotriacetates, ethylenediamine tetraproprionates triethylenetetraamine-hexaacetates diethylenetriaminepentaacetates, and ethanoldiglycines, alkali metal, ammonium, and substituted ammonium salts thereof and mixtures thereof.

Amino phosphonates are also suitable for use as chelating agents in the compositions of the invention when at least low levels of total phosphorus are permitted in detergent compositions. Suitable amino phosphonates for use in the inventive compositions and include ethylenediaminetetrakis (methylenephosphonates), nitrilotris (methylenephosphorates) and diethylenetriaminepentakis (methylenephosphonates). Preferably, these amino phosphonates do not contain alkyl or alkenyl groups with more than about 6 carbon atoms. Alkylene groups can be shared by substructures.

Polyfunctionally-substituted aromatic chelating agents are also useful in the compositions herein. U.S. Pat. No. 3,812,044, issued May 21, 1974, to Connor et al, incorporated herein by reference, discloses polyfunctionally-substituted aromatic chelating and sequestering agents. Preferred compounds of this type in acid form are dihydroxydisulfobenzenes such as 1,2dihydroxy-3,5-disulfobenzene. Alkaline detergent compositions can contain these materials in the form of alkali metal, ammonium or substituted ammonium (e.g. mono- or triethanol-amine) salts.

If utilized, these chelating agents will generally comprise from about 0.1% to about 10% by weight of the detergent compositions herein. More preferably chelating agents will comprise from about 0.1% to about 3.0% by weight of such compositions.

The compositions of the present invention can also optionally contain water-soluble ethoxylated amines having clay soil removal and anti-redeposition properties. Granular detergent compositions which contain these compounds typically contain from about 0.01% to about 10.0% by weight of the water-soluble ethoxylated amines; liquid detergent compositions, typically about 0.01% to about 5%.

These compounds are selected preferably from the group consisting of:

(1) ethoxylated monoamines;

(2) ethoxylated diamines;

(3) ethoxylated polyamines;

(4) ethoxylated amine polymers; and (5) mixtures thereof.

The most preferred soil release and anti-redeposition agent is ethoxylated tetraethylanepentamine. Exemplary ethoxylated amines are further described in U.S. Pat. No. 4,597,898, VanderMeer, issued Jul. 1, 1986, incorporated herein by reference. Another group of preferred clay soil removal/antiredeposition agents are the cationic compounds disclosed in European Patent Application 111,965, Oh and Gosselink, published Jun. 27, 1984, incorporated herein by reference. Other clay soil removal/antiredeposition agents which can be used include the ethoxylated amine polymers disclosed in European Patent Application 111,984, Gossellink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985, all of which are incorporated herein by reference.

Other clay soil removal and/or anti redeposition agents known in the art can also be utilized in the compositions hereof. Another type of preferred anti-redeposition agent includes the carboxy methyl cellulose (CMC) materials. These materials are well known in the art.

Polymeric dispersing agents can advantageously be utilized in the compositions hereof. These materials can aid in calcium and magnesium hardness control. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particular soil release peptization, and anti-redeposition.

Polycarboxylate materials which can be employed as the polymeric dispersing agent herein can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein of monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967. This patent is incorporated herein by reference.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000 most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, which publication is incorporated herein by reference.

Another polymeric material which can be included is polyethylene glycol (PEG). PEG can exhibit dispersing agent performance as well as act as a clay soil removal/antiredeposition agent. Typical molecular weight ranges for these purposes range from about 500 to about 100,000 preferably from about 1,000 to about 50,000, more preferably from about 1,500 to about 10,000.

Any optical brighteners or other brightening or whitening agents known in the art can be incorporated into the detergent compositions hereof.

The choice of brightener for use in detergent compositions will depend upon a number of factors, such as the type of detergent, the nature of other components present in the detergent composition, the temperatures of wash water, the degree of agitation, and the ratio of the material washed to tub size.

The brightener selection is also dependent upon the type of material to be cleaned, e.g., cottons, synthetics, etc. Since most laundry detergent products are used to clean a variety of fabrics, the detergent compositions should contain a mixture of brighteners which will be effective for a variety of fabrics. It is of course necessary that the individual components of such a brightener mixture be compatible.

Commercial optical brighteners which may be useful in the present invention can be classified into subgroups which include, but are not necessarily limited to, derivatives of stilbene, pyrazoline, cumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982), the disclosure of which is incorporated herein by reference.

Stilbene derivatives which may be useful in the present invention include, but are not necessarily limited to, derivatives of bis-(triazinyl)amino-stilbene; bisacylamino derivatives of stilbene; triazole derivatives of stilbene; oxadiazole derivatives of stilbene oxazole derivatives of stilbene; and styryl derivatives of stilbene. Certain derivatives of bis(triazinyl)aminostilbene which may be useful in the present invention may be prepared from 4,4'-diamine-stilbene-2,2'-disulfonic acid.

Coumarin derivatives which may be useful in the present invention include, but are not necessarily limited to, derivatives substituted in the 3-position, in the 7-position, and in the 3- and 7-positions.

Carboxylic acid derivatives which may be useful in the present invention include, but are not necessarily limited to, fumaric acid derivatives; benzoic acid derivatives; p-phenylenebis-acrylic acid derivatives; naphthalenedicarboxylic acid derivatives; heterocyclic acid derivatives; and cinnamic acid derivatives.

Cinnamic acid derivatives which may be useful in the present invention can be further subclassified into groups which include, but are not necessarily limited to, cinnamic acid derivatives, styrylazoles, styrylbenzofurans, styryloxadiazoles, styryltriazoles, and styrylpolyphenyls, as disclosed on page 77 of the Zahradnik reference.

The styrylazoles can be further subclassified into styrylbenzoxazoles, styrylimidazoles and styrylthiazoles, as disclosed on page 78 of the Zahradnik reference. It will be understood that these three identified subclasses may not necessarily reflect an exhaustive list of subgroups into which styrylazoles may be subclassified.

Another class of optical brighteners which may be useful in the present invention are the derivatives of dibenzothiophene-5,,5-dioxide disclosed at page 741–749 of *The Kirk-Othmer Encyclopedia of Chemical Technology,* Volume 3, pages 737–750 (John Wiley & Son, Inc., 1962), the disclosure of which is incorporated herein by reference, and include 3,7-diaminodibenzothiophene-2,8-disulfonic acid, 5,5 dioxide.

Another class of optical brighteners which may be useful in the present invention include azoles, which are derivatives of 5-membered ring heterocycles. These can be further subcategorized into monoazoles and bisazoles. Examples of monoazoles and bisazoles are disclosed in the *Kirk-Othmer* reference.

Another class of brighteners which may be useful in the present invention are the derivatives of 6-membered-ring heterocycles disclosed in the *Kirk-Othmer* reference. Examples of such compounds include brighteners derived from pyrazine and brighteners derived from 4-aminonaphthalamide.

In addition to the brighteners already described, miscellaneous agents may also be useful as brighteners. Examples of such miscellaneous agents are disclosed at pages 93–95 of the Zahradnik reference, and include 1-hydroxy-3,6,8-pyrenetrisuphonic acid; 2,4-dimethoxy-1,3,5-triazin-6-yl-pyrene; 4,5-diphenylimidazolonedisulphonic acid and derivatives of pyrazoline-quinoline.

Other specific examples of optical brighteners which may be useful in the present invention are those identified in U.S. Pat. No. 4,790,856, issued to Wixon on Dec. 13, 1988, the disclosure of which is incorporated herein by reference. These brighteners include the PHORWHITE series of brighteners from Verona. Other brighteners disclosed in this reference include: Tinopal UNPA, Tinopal CBS and Tinopal 5BM; available from Ciba-Geigy; Arctic White CC and Artic White CWD, available from Hilton-Davis, located in Italy; the 2-(4-styryl-phenyl)-2H-naphthol[1,2-d]triazoles; 4,4'-bis-(1,2,3-triazol-2-yl)-stilbenes; 4,4'-bis(styryl) bisphenyls; and the y-aminocoumarins. Specific examples of these brighteners include 4-methyl-7-diethylamino coumarin; 1,2-bis(-benzimidazol-2-yl)ethylene; 1,3-diphenylphrazolines; 2, 5-bis (benzoxazol-2-yl) thiophene; 2-styrylnaphth-[1,2-d]oxazole; and 2-(stilbene-4-yl)2-H-naphtho-[1,2-d]triazole.

Other optical brighteners which may be useful in the present invention include those disclosed in U.S. Pat. No. 3,646,015, issued Feb. 29, 1972, to Hamilton, the disclosure of which is incorporated herein by reference.

Compounds known, or which become known, for reducing or suppressing the formation of suds can be incorporated into the composition of the present invention. The incorporation of such materials, hereinafter "suds suppressors," can be desirable because the presence of anionic surfactants with polyhydroxy fatty acid amide surfactants hereof can increase suds stability of the detergent compositions. Suds suppression can be of particular importance when the detergent compositions include a relatively high sudsing surfactant in combination with the polyhydroxy fatty acid amide surfactants. Suds suppression is particularly desirable for compositions intended for use in front loading automatic washing machines. These machines are typically characterized by having drums, for containing the laundry and wash water, which have a horizontal axis and rotary action about the axis. This type of agitation can result in high suds formation and, consequently, in reduced cleaning performance. The use of suds suppressors can also be of particular importance under hot water washing conditions and under high surfactant concentration conditions.

A wide variety of materials may be used as suds suppressors in the compositions hereof. Suds suppressors are well known to those skilled in the art. They are generally described, for example, in Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acids and soluble salts thereof. The set materials are discussed in U.S. Pat. No. 2,954,347, issued Sep. 27, 1960 to Wayne St. John, said patent being incorporated herein by reference. The monocarboxylic fatty acids, and salts thereof, for use as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts. These materials are a preferred category of suds suppressor for detergent compositions.

The detergent compositions may also contain non-surfactant suds suppressors. These include, for example, high molecular weight hydrocarbons such as paraffin, fatty acid esters (e.g., fatty acid triglycerides), fatty acid esters of monovalent alcohols, aliphatic $C_{18}$–$C_{41}$ ketones (e.g., stearone), etc. Other suds inhibitors include N-alkylated amino triazines such as trito hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 5° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo, et al. incorporated herein by reference. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors, comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganoxiloxane is chemisorbed or fused onto the silica. Silicone suds suppressors are well known in the art and are, for example, disclosed in U.S. Pat. No. 4,256,779, issued May 5, 1981 to Gandolfo et al. and European Patent Application No. 89307851.9, published Feb. 7, 1990, by Starch, M. S., both incorporated herein by reference.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933, 672, Bartolotta et al., and in U.S. Pat. No. 4,652,392, Baginiski et al., issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1500 cs. at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3SiO_{1/2}$ units and to $SiO_2$ units of from about 0.6:1 to about 1.2:1; and (iii) from about 1 to about 20 parts per 100 parts by weight of (i) of a solid silica gel.

For any detergent compositions to be used in automatic laundry washing machines, suds should not form to the extent that they overflow the washing machine. Suds suppressors, when utilized, are preferably present in a "suds suppressing amount." By "suds suppressing amount" is meant that the formulator of the composition can select an amount of this suds controlling agent that will sufficiently control the suds to result in a low-sudsing laundry detergent for use in automatic laundry washing machines.

The amount of suds control will vary with the detergent surfactants selected. For example, with high sudsing surfactants, relatively more of the suds controlling agent is used to achieve the desired suds control than the lesser foaming surfactants. In general, a sufficient amount of suds suppressor should be incorporated in low sudsing detergent compositions so that the suds that form during the wash cycle of the automatic washing machine (i.e., upon agitation of the detergent in aqueous solution under the intended wash temperature and concentration conditions) do not exceed about 75% of the void volume of washing machine's containment drum, preferably the suds do not exceed about 50% of said void volume, wherein the void volume is determined as the difference between total volume of the containment drum and the volume of the water plus the laundry.

The compositions hereof will generally comprise from 0% to about 5% of suds suppressor. When utilized as suds suppressors, monocarboxylic fatty acids, and salts thereof, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0% by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphates are generally utilized in amounts ranging from about 0.1% to about 2%, by weight, of the composition.

Hydrocarbon suds suppressors are typically utilized in amounts ranging from about 0.01% to about 5.0%, although higher levels can be used.

Other Ingredients

A wide variety of other ingredients useful in detergent compositions can be included in the compositions hereof, including other active ingredients, carriers, hydrotropes, processing aids, dyes or pigments, solvents for liquid formulations, etc.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., propylene glycol, ethylene glycol, glycerine, and 1,2-propanediol) can also be used.

The detergent compositions hereof will preferably be formulated such that during use in aqueous cleaning operations, the wash water will have a pH of between about 6.5 to about 11, preferably between about 7.5 and about 10.5. Liquid product formulations preferably have a pH between about 7.5 and about 9.5, more preferably between about 7.5 and about 9.0. Techniques for controlling pH at recommended usage levels include the use of buffers, alkalis, acids, etc., and are well known to those skilled in the art.

This invention further provides a method for improving the performance of detergents containing anionic, nonionic, and/or cationic surfactant, and detersive enzyme, by utilizing therein an enzyme performance-enhancing amount of the polyhydroxy fatty acid amide surfactant described above, typically at least about 1% of such surfactant.

This invention further provides a method for cleaning substrates, such as fibers, fabrics, hard surfaces, skin, hair etc., by contacting said substrate, with a detergent composition comprising detersive enzyme and one or more anionic, nonionic, or cationic surfactants wherein said detergent composition contains an enzyme performance-enhancing amount of polyhydroxy fatty acid amide, typically at least about 1% by weight, of the composition, in the presence of a solvent such as water or water-miscible solvent (e.g., primary and secondary alcohols). Agitation is preferably provided for enhancing cleaning. Suitable means for providing agitation include rubbing by hand or preferably with use of a brush, sponge, cloth, mop, or other cleaning device, automatic laundry washing machines, automatic dishwashers, etc.

Mixtures of lipases, proteases, cellulases, amylases and peroxidases are adequately stable in the presence of certain non-alkylbenzene sulfonate surfactant systems, such that effective, heavy-duty liquid detergents can be formulated. Indeed, the formulation of stable, liquid, enzyme-containing detergent compositions constitutes a highly advantageous and preferred embodiment afforded by the technology of the present invention. The preferred liquid compositions herein comprise up to about 2%, preferably about 0.0001% to about 1%, most preferably about 0.001% to about 0.5%, on an active basis, of detersive enzyme. These enzymes are preferably selected from the group consisting of protease (preferred), lipase (preferred), amylase, cellulose, peroxidase, and mixtures thereof. Preferred are compositions with two or more classes of enzymes, most preferably where one is a protease.

While various descriptions of detergent proteases, cellulases, etc., are available in the literature, detergent lipases may be somewhat less familiar. Accordingly, to assist the formulator, lipases of interest include Amano AKG and Bacillis Sp lipase (e.g., Solvay enzymes). Also, see the lipases described in EP A 0 399 681, published November 28, 1990, EP A 0 218, 272, published Apr. 15, 1987 and PCT/US/ 88/00177, published May 18, 1989, all incorporated herein by reference.

Suitable fungal lipases include those producible by *Humicola lanuginosa* and *Thermoncyes lanuginosus*. Most preferred is the lipase obtained by cloning the gene from *Humicola lanuginosa* and expressing the gene in *Aspergillus oryzae,* as described in European Patent Application 0 258 058, incorporated herein by reference, commercially available under the trade name Lipolase.

From about 2 to about 20,000, preferably about 10 to about 6,000, lipase units of lipase per gram (LU/g) of product can be used in these compositions. A lipase unit is that amount of lipase which produces 1 $\mu$mol of titratable butyric acid per minute in a pH stat, where pH is 7.0, temperature is 30° C., and substrate is an emulsion tributyrin and gum arabic, in the presence of $C_a^{++}$ and NaCl in phosphate buffer.

Representative enzymes for use in the invention include those shown below.

Classes of detergent enzymes

| Enzyme Class | Substrate | Examples |
|---|---|---|
| Protease | Proteins: | Alcalase |
| | Blood | Savinase |
| | Egg | Esperase |
| | Grass | Durazyn |
| | Human soils | |
| Amylase | Starch: | BAN |
| | Cocoa | Termamyl |
| | Gravy | |
| | Oatmael | |
| | Pasta, etc. | |
| Lipase | Triglycerides: | Lipolase |
| | Vegetabie oils | |
| | Fats | |
| | Human sebum | |
| Cellulase | Cellulose: | Celluzyme |
| | Microfibrils causing greying, piling | |

All documents, e.g., patents and journal articles, cited above or below are hereby incorporated by reference in their entirety.

One skilled in the art will recognize that modifications may be made in the present invention without deviating from the spirit or scope of the invention. The invention is illustrated further by the following examples which are not to be construed as limiting the invention or scope of the specific procedures described herein.

In the following examples, all amounts are stated in percent by weight of active material unless indicated otherwise.

EXAMPLE A

MIXING PROCEDURE A

Laundry detergent formulations may be prepared by adding water to a suitable vessel equipped with mixing means. The remaining ingredients are added in the order in which they are listed in the formulations set forth in the following examples. The resulting mixtures are continuously mixed until a liquid of uniform consistency is obtained. The pH may be adjusted as needed to about 8.5–8.8 using suitable alkaline or acidic reagents.

MIXING PROCEDURE B

Alternatively, laundry detergent formulations may be prepared by adding water to a suitable vessel equipped with mixing, heating and cooling means, followed by the remaining ingredients in the order in which they are listed in the formulations set forth in the following examples. The resulting mixtures are heated to about 140–145° F. and mixed until a liquid of uniform consistency is obtained. The pH may be adjusted as required to about 8.5–8.8 using suitable alkaline or acidic reagents.

EXAMPLE B

Test Conditions for Determination of Detergency

The test conditions for determining the detergency for formulations set forth in the following examples are shown below Results for detergency are expressed as the change in reflectance for fabric before and after washing, ΔR. In a detergency determination, a higher ΔR value indicates better cleaning of a fabric swatch and, thus, a better detergent composition.

Warm Wash

Temperature of washing solution: 100° F.

Washing Time: 10 minutes.

Temperature of rinse water: 80° F.

Rinsing time: 5 minutes.

Water hardness: 140 ppm.

Soil: dust-sebum.

Agitation: 100 rpm.

Cold Wash

Temperature of washing solution 60° F.

Temperature of rinse water 60° F.

All other parameters are the same as used for the warm wash detergency determination.

EXAMPLE C

Test Conditions for Determination of Antiredeposition

The test conditions for determining the antiredeposition efficacy for formulations set forth in the following examples are shown below. Results for antiredeposition efficacy are expressed as the change in reflectance for fabric before and after washing, i.e., ΔR=refectance before washing—reflectance after washing.

Reflectance is measured for three (3) sets of clean sample 3"×4" swatches (3 cotton, 3 cotton/polyester and 3 polyester).

Three (3) soiled (dust-sebum or clay) swatches and 3 clean swatches of each fabric type are washed together using the following conditions at 0.2% detergent concentration[1]. Washing is repeated 3 times in the same surfactant solution, each time introducing a new set of 3 soiled swatches with the original set of clean swatches while removing the washed soiled swatches. Reflectance determinations are then made for original set of clean swatches. In redeposition determinations, lower ΔR values indicate less redeposition of soil onto a fabric swatch and, thus, better antiredeposition agents.

[1] Detergent concentration equals total surfactant concentration. Surfactant concentration does not include non-surfactants such as traditional hydrotropes.

Warm Wash

Temperature of washing solution: 100° F.

Washing cycle: 10 minutes.

Temperature of rinse water: 80° F.

Rinsing cycle: 5 minutes.

Water hardness: 140 ppm.

Agitation: 100 rpm.

Cold Wash

Temperature of washing solution 60° F.

Temperature of rinse water 60° F.

All other parameters are the same as used for the warm wash detergency determination.

EXAMPLE 1

| | Formulation No. | | | | | | |
|---|---|---|---|---|---|---|---|
| Components | 1 | 2 | 3 | 4 | 5 | 6 | 7 |
| Alpha-Step MC-48[2] | 18.08 | | | | 10.07 | 10.07 | 10.07 |
| Sodium Lauryl Sulfate | | 18.08 | | | 8.00 | | |
| Sodium Lauryl (3E0) ether sulfate | | | 18.08 | | | 8.00 | |
| Sodium LAS[3] | | | | 18.08 | | | 8.00 |
| Neodol 25-7[4] | 9.03 | 9.03 | 9.03 | 9.03 | 9.03 | 9.03 | 9.03 |
| TEA | 1.00 | 1.00 | 1.00 | 1.00 | 1.00 | 1.00 | 1.00 |
| DI Water | All are Q.S. to 100 | | | | | | |
| % Active Surfactant | 27.1 | 27.1 | 27.1 | 27.1 | 27.1 | 27.1 | 27.1 |
| Appearance | Clear | Clear | Clear | Clear | Clear | Clear | Clear |
| pH | 8.8 | 8.8 | 8.8 | 8.8 | 8.8 | 8.8 | 8.8 |
| CMC[5] | 29.0 | 41.0 | 30.4 | 50.0 | 28.6 | 28.4 | 28.4 |
| Detergency (change in reflectance, ΔR) Warm Wash Detergency Test Conditions | | | | | | | |
| 0.2% active surfactant | | | | | | | |
| Cotton Fabric | 16.1 | 15.4 | 13.9 | 16.3 | 17.4 | 17.4 | 18.1 |
| Cotton/poly. Fabric | 12.8 | 14.0 | 14.0 | 15.1 | 16.1 | 16.1 | 16.4 |
| 0.5% active surfactant | | | | | | | |
| Cotton Fabric | 18.8 | 16.4 | 16.5 | 18.2 | 18.7 | 18.4 | 20.1 |
| Cotton/poly. Fabric | 16.8 | 15.5 | 14.6 | 15.0 | 17.7 | 16.7 | 17.9 |
| Cold Wash Detergency Test Conditions | | | | | | | |
| 0.2% active surfactant | | | | | | | |
| Cotton Fabric | 17.8 | 18.2 | 16.8 | 16.4 | 20.3 | 19.8 | 18.1 |
| Cotton/poly. Fabric | 15.0 | 13.5 | 14.3 | 13.6 | 15.4 | 16.2 | 15.5 |
| 0.5% active surfactant | | | | | | | |
| Cotton Fabric | 18.4 | 19.0 | 18.7 | 20.4 | 20.7 | 20.8 | 21.9 |
| Cotton/poly. Fabric | 15.7 | 14.2 | 16.2 | 15.6 | 15.9 | 17.9 | 17.3 |

-continued

[2]Sodium salt of methyl ester of α-sulfonated fatty $C_{12-14}$ acid and Disodium salt of α-sulfonated $C_{12-14}$ fatty acid, mono:di ratio of about 5:1

[3]Linear alkyl benzene sulfonate having an average of 11.5 carbon atoms in alkyl portion.

[4]$C_{12-15}$ alcohol ethoxylated with 7 moles of ethylene oxide.

[5]Critical micelle concentration (mg of surfactant/mL).

EXAMPLE 2

| | Formulation No. | | |
|---|---|---|---|
| Components | 8 | 9 | 10 |
| DI Water | Q.S. to 100.00 | Q.S. to 100.00 | Q.S. to 100.00 |
| Sodium Sulfate | 2.00 | 2.00 | 2.00 |
| Alpha-Step MC-48 | 12.30 | 12.30 | 12.30 |
| Na[6] Lauryl (3) Ether Sulfate | 19.90 | | |
| Na LAS | | 19.90 | |
| Na Lauryl Sulfate | | 19.90 | |
| Neodol 25-7 | 22.80 | 22.90 | 22.90 |
| TEA 99% | 2.00 | 2.00 | 2.00 |
| weight % Active Surfactant | 55.0 | 55.0 | 55.0 |
| Appearance | Clear | Clear | Clear |
| Viscosity @ 25° C. (cps) | 550 | 460 | 500 |
| pH | 8.8 | 8.8 | 8.8 |
| Detergency @0.047% Active (change in reflectance, ΔR) Warm Wash Detergency Test Conditions | | | |
| Cotton Fabric | 15.6 | 13.2 | 14.2 |
| Cotton/Polyester Fabric | 13.2 | 11.2 | 12.5 |

[6]Na refers to Sodium.

EXAMPLE 3

| | Formulation No. | | | |
|---|---|---|---|---|
| Components | 11 | 12 | 13 | 14 |
| DI Water | Q.S. to 100.00 | Q.S. to 100.00 | Q.S. to 100.00 | Q.S. to 100.00 |
| Sodium Sulfate | 1.00 | 1.00 | 1.00 | 1.00 |
| TEA 99% | 1.00 | 1.00 | 1.00 | 1.00 |
| Alpha-Step MC-48 | 6.06 | 6.06 | 6.06 | 6.06 |
| Sodium $C_{12-15}$ (7E0) Ether Sulfate | 9.77 | | | |
| Sodium $C_{12-15}$ (5E0) Ether Sulfate | | 9.77 | | |
| Sodium lauryl ether (3E0) sulfate | | | 9.77 | 9.77 |
| Fatty acid (lauryl) methyl ester ethoxylated with 10.9 moles of ethylene oxide[7] | | | 11.27 | |
| Fatty acid (lauryl) methyl ester ethoxylated with 14.6 moles of | | | | 11.27 |

-continued

| Components | Formulation No. 11 | 12 | 13 | 14 |
|---|---|---|---|---|
| ethylene oxide[8] | | | | |
| Neodol 25-7 | 11.27 | 11.27 | | |
| % Active Surfactant | 27.10 | 27.10 | 27.10 | 27.10 |
| Appearance | Clear | Clear | Clear | Clear |
| Viscosity @ 25° C. (cpu) | 200 | 250 | 300 | 250 |
| pH | 8.8 | 8.8 | 8.8 | 8.8 |
| Detergency @0.047% Active (change in reflectance, ΔR) Warm Wash Detergency Test Conditions | | | | |
| Cotton Fabric | 17.0 | 16.1 | 16.1 | 16.5 |
| Cotton/Polyester Fabric | 15.4 | 14.8 | 13.9 | 14.0 |

[7]Compound has the following structure: $RCO_2(CH_2CH_2O)_nCH_3$ where R is lauryl and n is an average of 10.9.

[8]Compound has the following structure: $RCO_2(CH_2CH_2O)_nCH_3$ where R is lauryl and n is an average of 14.6.

EXAMPLE 4

| Components | Formulation No. 15 | 16 | 17 | 18 |
|---|---|---|---|---|
| DI Water | Q.S. to 100.00 | Q.S. to 100.00 | Q.S. to 100.00 | Q.S. to 100.00 |
| Sodium Sulfate | 1.00 | 1.00 | 1.00 | 1.00 |
| TEA 99% | 1.50 | 1.50 | 1.50 | 1.50 |
| Na Alpha Sulfonated Methyl Ester of $C_{12}$ Acid[9] | 14.53 | | | |
| Na Alpha Sulfonated Methyl Ester of $C_{12-14}$ Acid[10] | | 14.53 | | |
| Na Alpha Sulfonated Methyl Ester of $C_{14}$ Acid[11] | | | 14.53 | |
| Na Alpha Sulfonated Methyl Ester of $C_{16}$ Acid[12] | | | | 14.53 |
| Na Lauryl (3E0) Ether Sulfate | 11.75 | 11.75 | 11.75 | 11.75 |
| Neodol 25-7 | 11.40 | 11.40 | 11.40 | 11.40 |
| weight % active Surfactant | 37.68 | 37.68 | 37.68 | 37.68 |
| Appearance | Clear | Clear | Hazy | Opaque |
| Consistency @ 25° C. (cpa) | Flowing Liquid | Flowing Liquid | Paste | Gel/ Paste |
| pH | 8.8 | 8.8 | 8.8 | 8.8 |
| Detergency @0.047% Active (change in reflectance, ΔR) Warm Wash Detergency Test Conditions | | | | |
| Cotton Fabric | 14.7 | 15.6 | 15.4 | 15.5 |
| Cotton/Polyester Fabric | 13.5 | 14.5 | 13.8 | 14.0 |

[9]Contains disalt at mono:di ratio of about 5:1.

[10]Contains disalt at mono:di ratio of about 5:1.

[11]Contains disalt at mono:di ratio of about 5:1.

[12]Contains disalt at mono:di ratio of about 5:1.

EXAMPLE 5

| Components | Formulation No. 19 | 20 | 21 | 22 |
|---|---|---|---|---|
| DI Water | Q.S. to 100.00 | Q.S. to 100.00 | Q.S. to 100.00 | Q.S. to 100.00 |
| Sodium Sulfate | 1.00 | 1.00 | 1.00 | 1.00 |
| TEA 99% | 1.00 | 1.00 | 1.00 | 1.00 |
| Alpha-Step MC-48 | 6.01 | 6.01 | 6.01 | 6.01 |
| Na Lauryl (3E0) Ester Sulfate | 9.77 | 9.77 | 9.77 | 9.77 |
| Neodol 25-7 | 11.27 | 11.27 | 11.27 | 11.27 |
| Coco ($C_{12-14}$) Fatty Acid Soap, Na Salt | 5.00 | | | |
| DC Silicone Antifoam 1430 | | 0.50 | | |
| Pluronic P104[13] | | | 5.00 | |
| Pluronic 17R4[11] | | | | 5.00 |
| % Active Surfactant | 32.1 | 27.1 | 32.1 | 32.1 |
| Appearance | Clear | Clear | Clear | Clear |
| pH | 8.8 | 8.8 | 8.8 | 8.8 |

[13]Polyoxyethylene, polyoxypropylene block copolymer identifed by the Cosmetics, Toiletry, and Fragrance Association as Ploxamer 334, commercially available from BASF as Pluracare/Pluronic P104.

[14]Polyoxyethylene, polyoxypropylene block copolymer identifed by the Cosmetics, Toiletry, and Fragrance Association as Ploxamer 334, commercially available from BASF as Pluracare/Pluronic 17R4.

EXAMPLE 6

Shake Foam Test

Procedure:

1. Prepare a 0.2% active solution of the sample liquid detergent material in 140 ppm hardness tap water at 25 deg C.

2. Introduce 100 g of the 0.2% solution into a 500 ml graduated cylinder, keeping foam to a minimum.

3. Shake the cylinder 20 complete times using an automatic shake foam machine capable of keeping speed and force constant.

4. Let foam settle for 5 seconds, then measure total height in ml, including the base of 100 ml of solution.

5. Repeat steps 1–5 seven (7) times.

The sample liquid detergent material employed in this example is Formulation 20 from Example 5 above.

| Total Number of Shakes | Foam height (ml) |
|---|---|
| 20 | 100 |
| 40 | 100 |
| 60 | 100 |
| 80 | 100 |
| 100 | 115 |
| 120 | 115 |
| 140 | 120 |
| 160 | 120 |

| | Formulation No. | | | | |
|---|---|---|---|---|---|
| | 1 | 2 | 3 | 4 | 5 |
| Sodium lauryl sulfate | 18.0 | 9.0 | | | |
| Sodium lauryl ether sulfate (3 moles of ethylene oxide) | | | 18.0 | 9.0 | |
| $C_{11.5\ (average)}$ alkyl benzene sulfonate | | | | | 18.0 |
| $C_{12-15}$ linear alcohol ethoxyate (7 moles of ethylene oxide) | 9.0 | 9.0 | 9.0 | 9.0 | 9.0 |
| methyl ester of alpha sulfonated $C_{12-14}$ fatty acid, sodium salt[15] | | 9.0 | | 9.0 | |
| deionized water | Q.S. to 100% | Q.S. to 100% | Q.S to 100% | Q.S. to 100% | Q.S. to 100% |
| pH | 8.8 | 8.8 | 8.8 | 8.8 | 8.8 |
| appearance | clear | clear | clear | clear | clear |

| | Formulation No. | | | |
|---|---|---|---|---|
| | 6 | 7 | 8 | 9 |
| Sodium lauryl ether sulfate (3 moles of ethylene oxide) | | 18.0 | 16.0 | 8.0 |
| $C_{11.5\ (average)}$ alkyl benzene sulfonate | 9.0 | | | |
| $C_{12-15}$ linear alcohol ethoxyate (7 moles of ethylene oxide) | 9.0 | 9.0 | | |
| 75:25 mixture of $C_{12/14}$ N-methyl glucamide | | | 11.0 | 11.0 |
| methyl ester of alpha sulfonated $C_{12-14}$ fatty acid, sodium salt[16] | 9.0 | | | 8.0 |
| disalt of alpha sulfonated $C_{12-14}$ fatty acid | | 2.0 | | |
| sodium xylene sulfonate | | | 3.0 | |
| deionized water | Q.S. to 100% | Q.S. to 100% | Q.S. to 100% | Q.S. to 100% |
| pH | 8.8 | 8.8 | 8.8 | 8.8 |
| appearance | clear | clear | clear | clear |

[15]Contains disalt of alpha sulfonated $C_{12-14}$ fatty acid at a ratio of methyl ester to disalt of about 5:1.
[16]Contains disalt of alpha sulfonated $C_{12-14}$ fatty acid at a ratio of methyl ester to disalt of about 5:1.

EXAMPLE 8

| | Formulation No. | | | | | | | | |
|---|---|---|---|---|---|---|---|---|---|
| | 1 | 2 | 3 | 4 | 5 | 6 | 7 | 8 | 9 |
| Antiredeposition Efficacy (change in reflectance, ΔR) | | | | | | | | | |
| Warm Wash Anti-Redeposition Test Conditions | | | | | | | | | |
| 0.2% active surfactant | | | | | | | | | |
| Cotton/Poly. Fabric | 3.6 | 1.8 | 3.9 | 1.9 | 3.5 | 2.0 | 2.0 | | |
| Polyester Fabric | 3.4 | 2.5 | 4.4 | 3.5 | 4.1 | 2.9 | 2.2 | | |
| Cold Wash Anti-Redeposition Test Conditions | | | | | | | | | |
| 0.2% active surfactant | | | | | | | | | |
| Cotton/poly. Fabric | | | 1.8 | 1.0 | 1.8 | 1.4 | 0.8 | 2.0 | 1.5 |
| Polyester Fabric | | | 2.0 | 1.5 | 2.3 | 2.0 | 1.3 | 2.7 | 2.4 |

EXAMPLE 9

| | Formulation No. | | | | |
|---|---|---|---|---|---|
| | 10 | 11 | 12 | 13 | 14 |
| Sodium lauryl ether sulfate (3 moles of ethylene oxide) | | | 27.0 | | 13.5 |
| $C_{11.5\ (average)}$ alkyl benzene sulfonate | 27.0 | | | 13.5 | |
| Sodium salt of α-sulfonated methyl ester of $C_{12-14}$ fatty acid | | 27.0 | | 13.5 | 13.5 |
| Deionized water | Q.S. to 100.0% | Q.S. to 100.0% | Q.S. to 100.0% | Q.S. to 100.0% | Q.S. to 100.0% |
| Antiredeposition Efficacy (change in reflectance, ΔR) | | | | | |
| Warm Wash Anti-Redeposition Test Conditions | | | | | |
| 0.2% active surfactant | | | | | |
| Cotton/poly. Fabric | 4.3 | 3.7 | 3.5 | 3.7 | 3.0 |
| Polyeater Fabric | 5.4 | 4.2 | 3.7 | 4.5 | 3.8 |
| Cold Wash Anti-Redeposition Test Conditions | | | | | |
| 0.2% active surfactant | | | | | |
| Cotton/poly. Fabric | 4.5 | 4.1 | 3.3 | 3.8 | 3.1 |
| Polyester Fabric | 5.8 | 4.5 | 3.7 | 5.1 | 3.9 |

From the foregoing it will be appreciated that, although specific embodiments of the invention have been described herein for purposes of illustration, various modifications may be made without deviating from the spirit and scope of the invention.

What is claimed is:

1. A detergent composition comprising:

(a) from about 2 to 35% of an α-sulfonated alkyl ester of a fatty acid having an average of about 12–16 carbon atoms;

(b) from about 2% to 25% by weight of a second anionic surfactant the second anionic surfactant being selected from alkyl ether sulfates, alkyl sulfates, linear alkyl benzene sulfonates, or mixtures thereof; and (c) from about 2.0 to 40% by weight of a nonionic surfactant, the sum of the concentrations of α-sulfonated alkyl ester, anionic surfactant, and nonionic surfactant in a washing solution being from about 0.05% to about 3.0% by weight.

2. A detergent according to claim 1, where the alkyl ester is an alpha sulfonated methyl ester of a fatty acid having an average of about 12–16 carbon atoms.

3. A detergent composition according to claim 2, wherein the second anionic surfactant and nonionic surfactant are present in the composition at a weight ratio of from about 4:1 to 1:3.

4. A detergent composition according to claim 3, wherein the nonionic surfactant is a $C_{8-18}$ fatty alcohol ethoxylate, ethoxylated alkyl phenol, ethoxylated methyl ester, alkyl polyglycoside or alkyl n-methyl glucamides.

5. A detergent composition according to claim 4, wherein the alkyl ester is present in the composition in an amount of from about 2–20% by weight of the composition.

6. A detergent composition according to claim 5, wherein the nonionic surfactant is present in an amount from about 8 to 20% by weight of the composition.

7. A detergent according to claim 1, where the composition is a liquid having a viscosity of from about 150–1000 cps at 25° C.

8. A detergent composition according to claim 1, where the alkyl ester is present in the formulation at a concentration of about 5–20% by weight.

* * * * *